(12) United States Patent
Kucharczyk

(10) Patent No.: US 7,158,608 B2
(45) Date of Patent: Jan. 2, 2007

(54) X-RAY DIFFRACTION APPARATUS

(75) Inventor: Damian Kucharczyk, Wroclaw (PL)

(73) Assignee: Oxford Diffraction Limited, Oxfordshire (GB)

( * ) Notice: Subject to any disclaimer, the term of this patent is extended or adjusted under 35 U.S.C. 154(b) by 56 days.

(21) Appl. No.: 10/442,914

(22) Filed: May 20, 2003

(65) Prior Publication Data

US 2004/0028180 A1    Feb. 12, 2004

(30) Foreign Application Priority Data

May 21, 2002 (GB) ................................. 0211691.1

(51) Int. Cl.
*G01N 23/20* (2006.01)
(52) U.S. Cl. ........................................ 378/71; 378/147
(58) Field of Classification Search .................. 378/71, 378/84, 85, 147
See application file for complete search history.

(56) References Cited

U.S. PATENT DOCUMENTS

| 4,322,618 | A | * | 3/1982 | Jenkins | ........................ | 378/84 |
| 4,780,903 | A | * | 10/1988 | Soezima | ..................... | 378/145 |
| 4,951,304 | A | * | 8/1990 | Piestrup et al. | ............ | 378/119 |
| 5,001,737 | A | * | 3/1991 | Lewis et al. | ................ | 378/147 |
| 5,245,648 | A | | 9/1993 | Kinney et al. | | |
| 5,579,363 | A | | 11/1996 | Ingal et al. | | |
| 5,747,821 | A | * | 5/1998 | York et al. | ............... | 250/505.1 |
| 5,778,039 | A | | 7/1998 | Hossain et al. | | |
| 5,987,095 | A | * | 11/1999 | Chapman et al. | ............ | 378/70 |
| 6,307,917 | B1 | * | 10/2001 | Shimizu et al. | ............ | 378/145 |
| 6,577,705 | B1 | * | 6/2003 | Chang et al. | ................. | 378/45 |
| 6,882,739 | B1 | * | 4/2005 | Kurtz et al. | ................ | 382/109 |
| 2001/0036250 | A1 | | 11/2001 | Hartrick et al. | | |

FOREIGN PATENT DOCUMENTS

EP        0 539 608 A1    5/1993

OTHER PUBLICATIONS

Thiel, Daniel J. et al. "Production of Intense Micrometer—sized x-ray beams of tapered glass microcapillaries" Rev. Sci. Instrum. 64 (10), Oct. 1993.*
WPI Acc. No. 1997-406543[38] & JP 09-0178674 A (Rigaku), Jul. 11, 1997.
*Patent Abstracts of Japan*, JP 63-0225159 A (Okada Yasumasa) Sep. 20, 1998.
*Patent Abstracts of Japan*, JP 05-0010892 A1, (Tanpaku Kougaku) Jan. 19, 1993.
*Patent Abstracts of Japan*, vol. 1997, No. 8, Aug. 29, 1997 (JP 09 089813 A).

* cited by examiner

*Primary Examiner*—Edward J. Glick
*Assistant Examiner*—Thomas R. Artman
(74) *Attorney, Agent, or Firm*—Kenyon & Kenyon LLP

(57) ABSTRACT

An x-ray diffraction apparatus comprises an x-ray source for generating an x-ray beam, a monochromator for generating a monochromatic x-ray beam from the x-ray beam, and a collimator for collimating the monochromatic x-ray beam and directing it onto a sample, wherein the x-ray source and the monochromator are pre-assembled and fixed with respect to each other in an integrated unit such that in use the path length of the x-ray beam from the source to the monochromator is maintained substantially constant. X-ray flux at the sample is further enhanced by use of a partial monocapillary collimator arranged to direct part of the X-ray beam to the sample by a single grazing reflection.

16 Claims, 15 Drawing Sheets

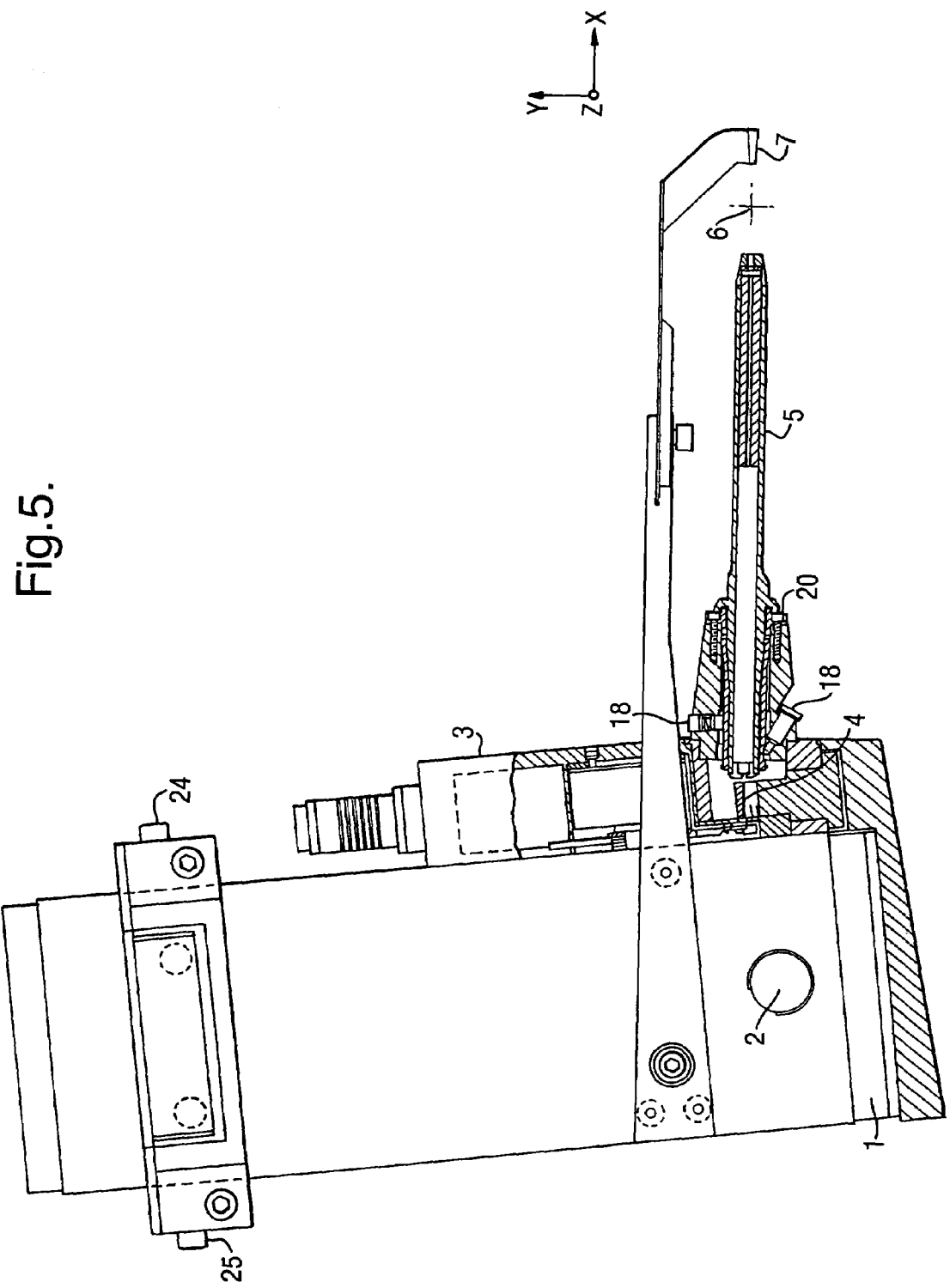

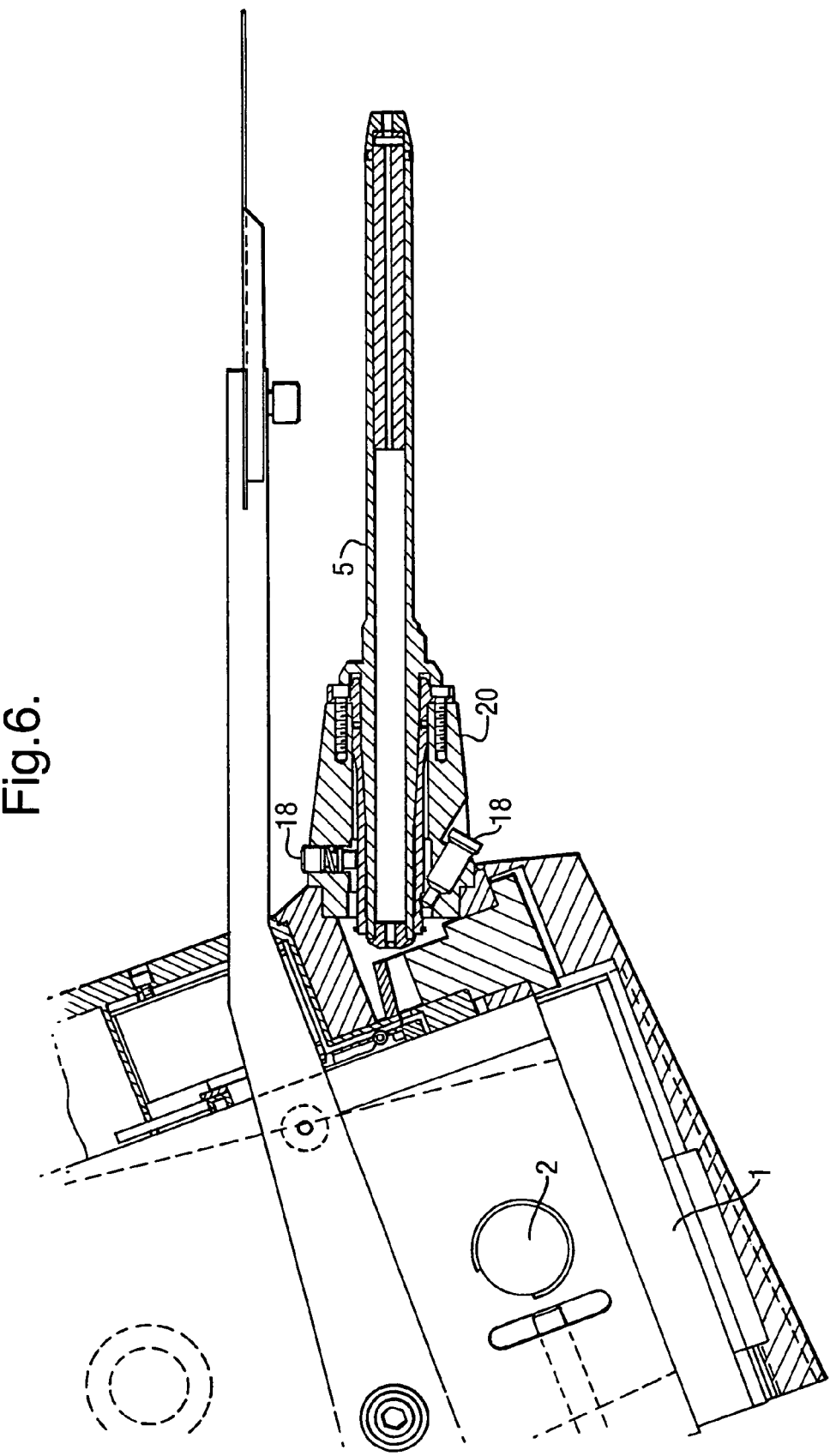

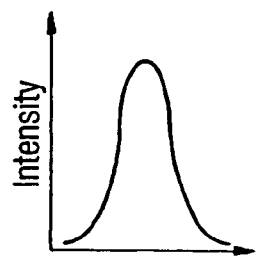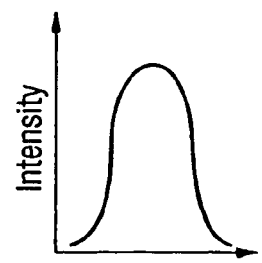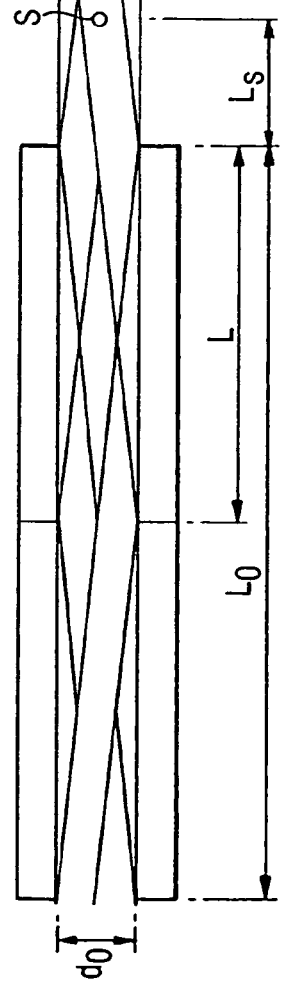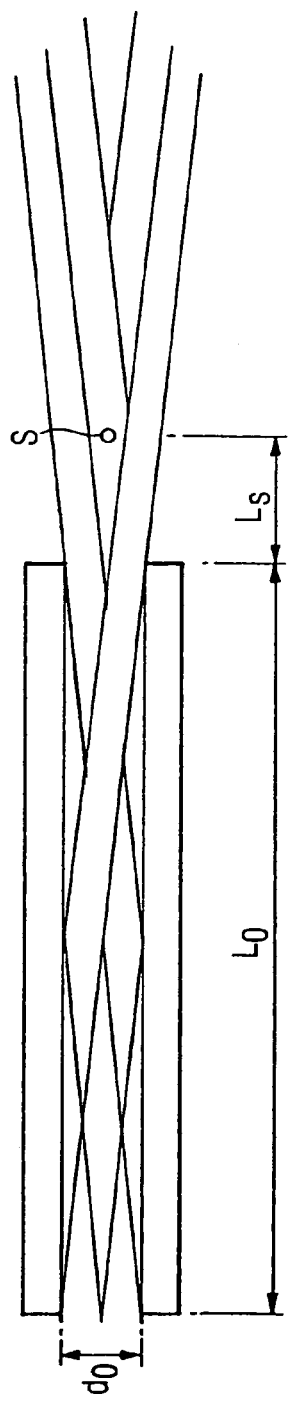

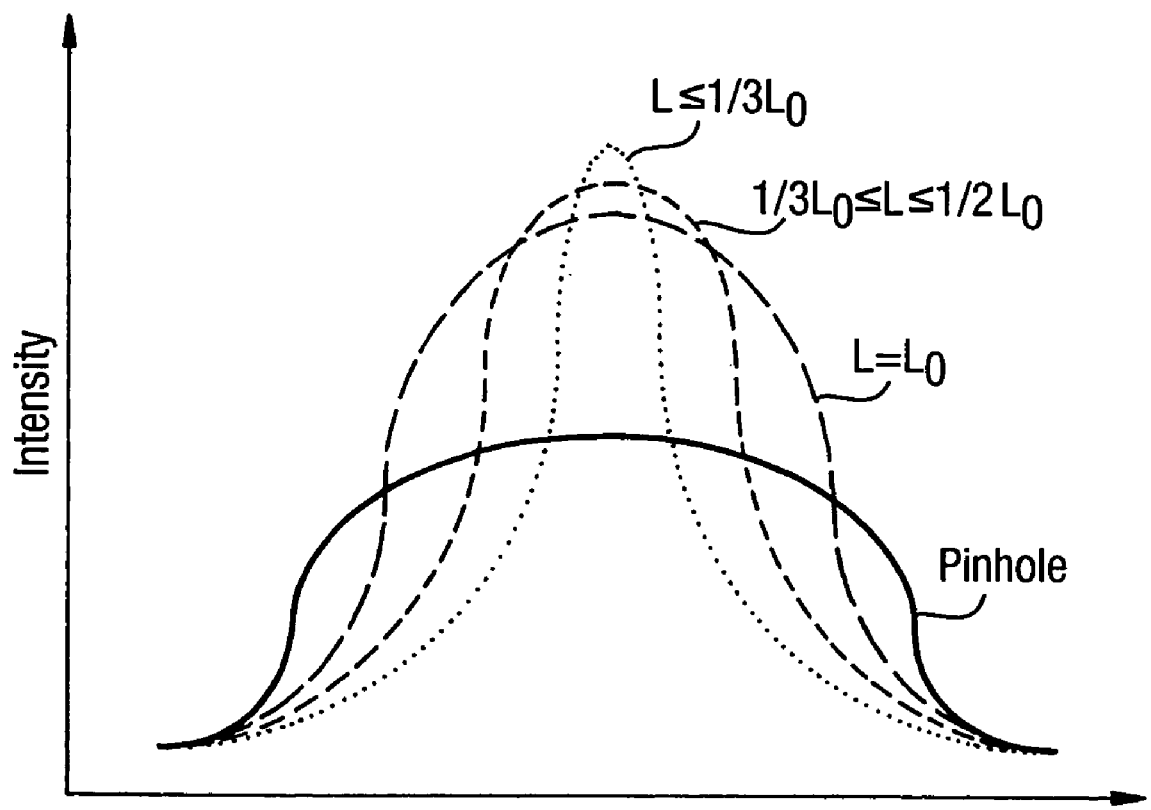

| | | dc/mm | | | | |
|---|---|---|---|---|---|---|
| | | 30 | 60 | 90 | 120 | 150 |
| REF 0.5mm | | | | | | |
| ENOX 0.5mm | | | | | | |

| | | dc/mm | | | | |
|---|---|---|---|---|---|---|
| | | 30 | 60 | 90 | 120 | 150 |
| REF 0.8mm | | | | | | |
| ENOX 0.8mm | | | | | | |

X-RAY DIFFRACTION APPARATUS

FIELD OF THE INVENTION

X-ray diffraction is an analytical technique for obtaining information on the structure of atoms or molecules in a crystal from the diffraction pattern which is produced by diffraction of x-rays by the crystal's atomic planes. The present invention concerns an improved apparatus for x-ray diffraction, and particularly an improved optics set up for increasing the maximum flux which can be obtained from an x-ray source.

BACKGROUND TO THE INVENTION

An x-ray diffraction apparatus typically includes an x-ray source which comprises a sealed tube including an electron gun and a target such as molybdenum or copper which generates x-rays when bombarded with electrons from the electron gun. The x-rays emerge from a pin hole in the sealed source unit, and a separate shutter unit is generally located adjacent the source unit to isolate the source unit when necessary for safety reasons. The shutter unit is located between the source and a monochromator. The x-ray source typically generates a wide spectrum of frequencies, and the monochromator is a filter provided to filter the x-rays to obtain a beam of a single frequency for irradiating the sample. A collimator comprising a metal tube collimates and directs the beam at the sample. The collimator controls the flux and divergence of the beam incident on the sample.

The source and shutter are typically mounted and the source is rotatable about an axis. The source and shutter are also moveable along the axis of rotation. The source can thereby be moved to vary its attack angle and maximise the flux which is incident on the sample. However, once the source has been adjusted to the optimum position for maximum flux, it is then necessary to align the monochromator and collimator to direct the flux onto the sample. The collimator must be aligned in two directions, and must be angled correctly. The known system is difficult to adjust accurately and reliably, due to the large number of different variables to be adjusted to obtain the optimum flux on the sample.

SUMMARY OF THE INVENTION

According to the present invention, an x-ray diffraction apparatus comprises:

an x-ray source for generating an x-ray beam;

a monochromator for generating a monochromatic x-ray beam from the x-ray beam generated by the x-ray source; and, a collimator for collimating the monochromatic x-ray beam and directing it onto a sample, wherein the x-ray source and the monochromator are pre-assembled and fixed with respect to each other in an integrated unit such that in use the path length of the x-ray beam from the source to the monochromator is maintained substantially constant The arrangement of the present invention has the advantage of compactness, thereby minimising the distance between the x-ray source and the monochromator and the distance between the monochromator and the sample. This reduces the loss of collection of x-ray flux due to beam divergence.

The arrangement also has the advantage that fewer adjustments are required to maximise the flux of the x-ray beam and then direct the beam onto the sample. Adjustments can be carried out sequentially, without the need for iteration, in contrast to the prior art set up in which a change of one setting usually required a readjustment of all the other settings. The prior art arrangement thereby requires set up by a skilled technician.

Preferably, the apparatus is arranged such that the angle of incidence of the x-ray beam on the monochromator may be varied. This may be achieved by mounting the x-ray source such that it is rotatable about an axis passing through the monochromator, but preferably the monochromator is rotatable on an axis passing through it. By varying the angle of the monochromator with respect to the x-ray source, fine adjustments may be achieved to maximise the flux of the monochromatic x-ray beam which is generated by the monochromator.

Preferably, for safety reasons, the integrated unit also includes a shutter located between the x-ray source and the monochromator such that the x-ray source can be isolated.

Preferably, the collimator is mounted such that the angle of the longitudinal axis of the collimator is variable with respect to the monochromator.

Preferably, this angle can be varied in two orthogonal planes. The collimator is mounted such that the direction of its longitudinal axis passes substantially through the centre of the monochromator. This can be achieved by mounting the collimator in a socket in a collimator holder.

The flux of the x-ray beam can be maximised by two sets of adjustments. Firstly, the angle of incidence of the x-ray beam on the monochromator is varied. Then the angle of the collimator to the monochromator is varied.

Preferably, the collimator holder is also integrated with the unit comprising the source, the monochromator and the shutter. Once the flux of the x-ray beam has been maximised by the abovementioned two adjustments, the entire integrated unit can be moved to direct the beam from the collimator onto the sample.

Preferably, at least a portion of the collimator comprises a monocapillary collimator arranged such that an outer diverging region of the monochromatic x-ray beam is reflected only once from an internal surface of the monocapillary collimator so as to be directed to the sample position.

The use of a monocapillary collimator permits the collection of a diverging portion of the monochromatic x-ray beam, which would otherwise be lost. Grazing incidence reflection from the internal surface of the monocapillary allows this portion of the beam to be re-directed towards the sample and combine with that portion of the x-ray beam that passes straight through the collimator without reflection. As x-ray flux is lost with each bounce, it is thus preferable that the x-ray beam undergoes only a single reflection.

Preferably, the monocapillary section of the collimator is towards the end proximate the sample.

This arrangement avoids collection of that part of the x-ray beam which would reflect on entry into the collimator and thus experience a subsequent reflection further along the collimator, thereby contributing to an unwanted background flux surrounding the illuminated sample.

Preferably, the monocapillary section extends over less than half the total length of the collimator.

Thus, the present invention provides an X-ray apparatus which is largely pre-aligned and fixed in an integrated unit during manufacture. Subsequent adjustment and optimisa tion of the alignment can be performed in a simple, step-by-step manner. The compact nature of the unit maximises the collection of X-ray flux, which would otherwise be lost through beam divergence, and the use of a partial mono-capillary collimator further enhances the X-ray flux at the sample position whilst minimising unwanted background illumination.

BRIEF DESCRIPTION OF THE DRAWINGS

Examples of the prior art and the present invention will now be described in detail with reference to the accompanying drawings, in which:

FIG. 5 is a top view with partial cross-section of an arrangement in accordance with the present invention;

FIG. 6 is a cross-section of the collimator mounting;

FIGS. 7A and 7B illustrate two monocapillary geometries; and

FIG. 8 shows intensity profiles at the sample position for different monocapillary geometries;

DETAILED DESCRIPTION

Figure 1:
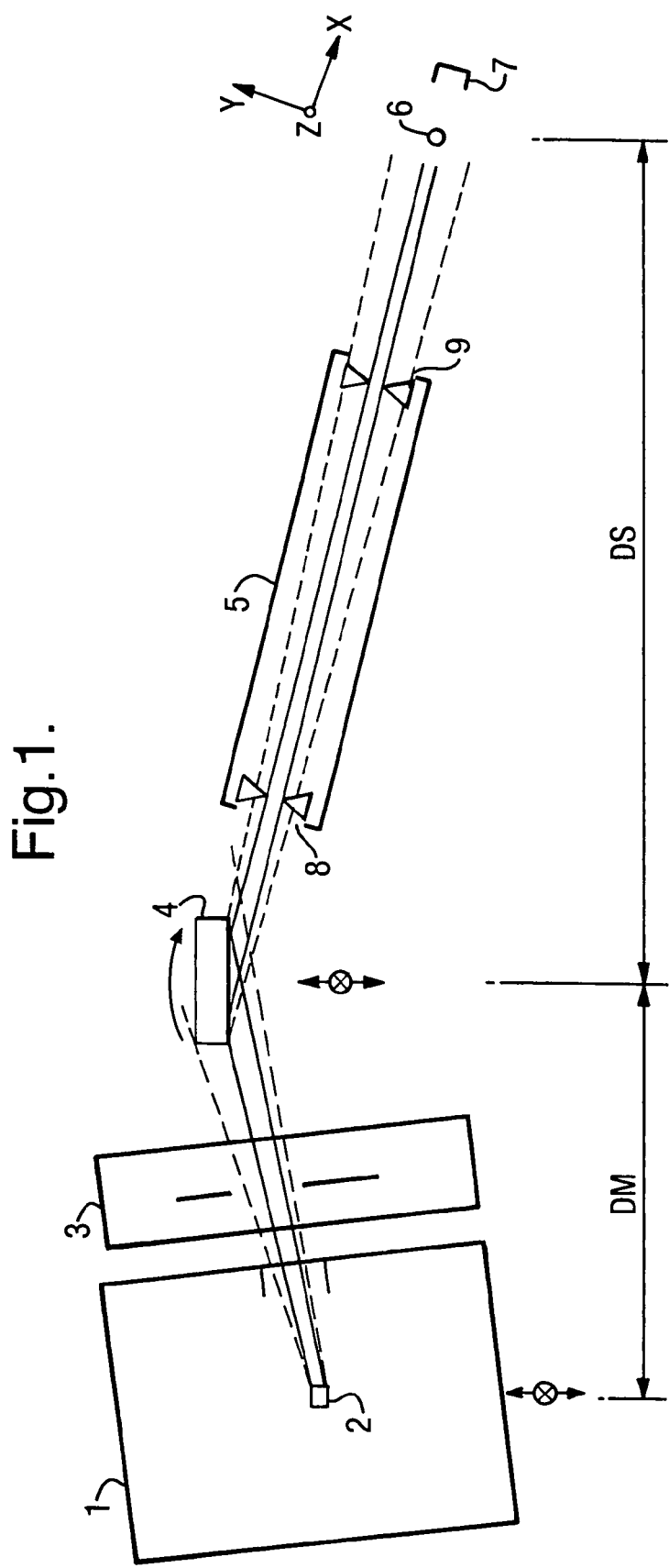
FIG. 1 is a top schematic view of a prior art x-ray optics arrangement.
Figure 2:
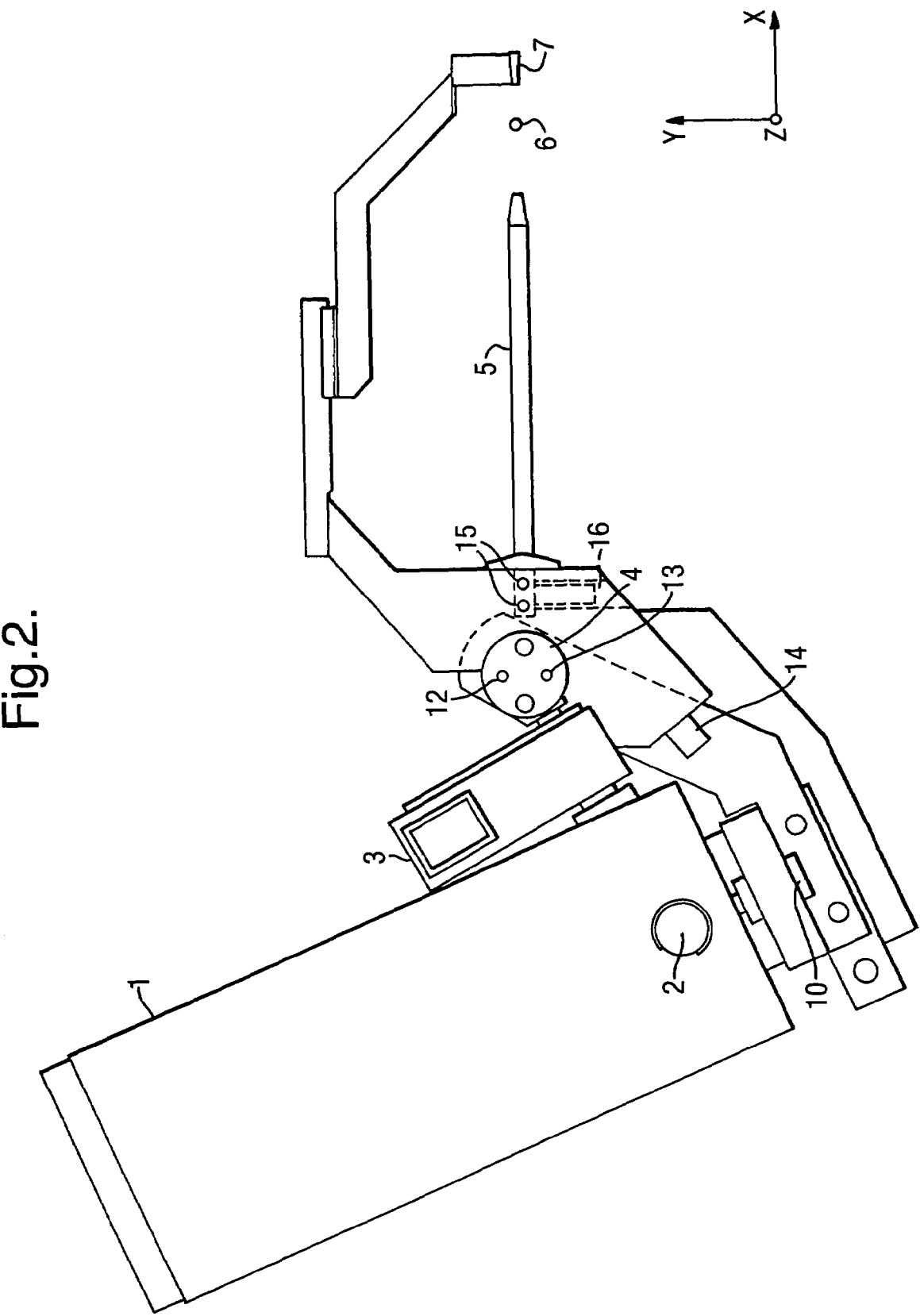
FIG. 2 is a side view of a prior art x-ray optics arrangement.
Figure 3:
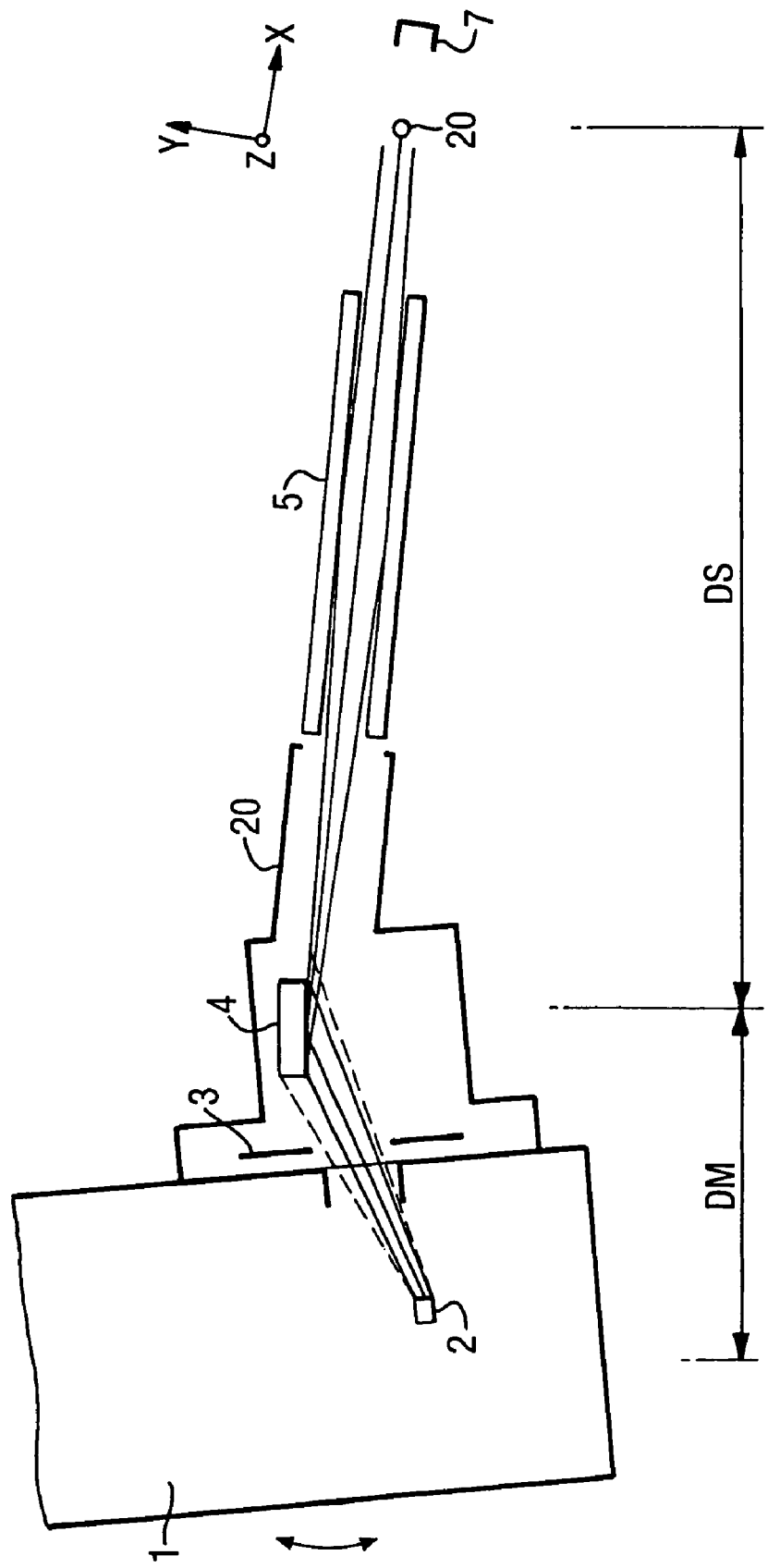
FIG. 3 is a top schematic view of an arrangement in accordance with the present invention.
Figure 4:
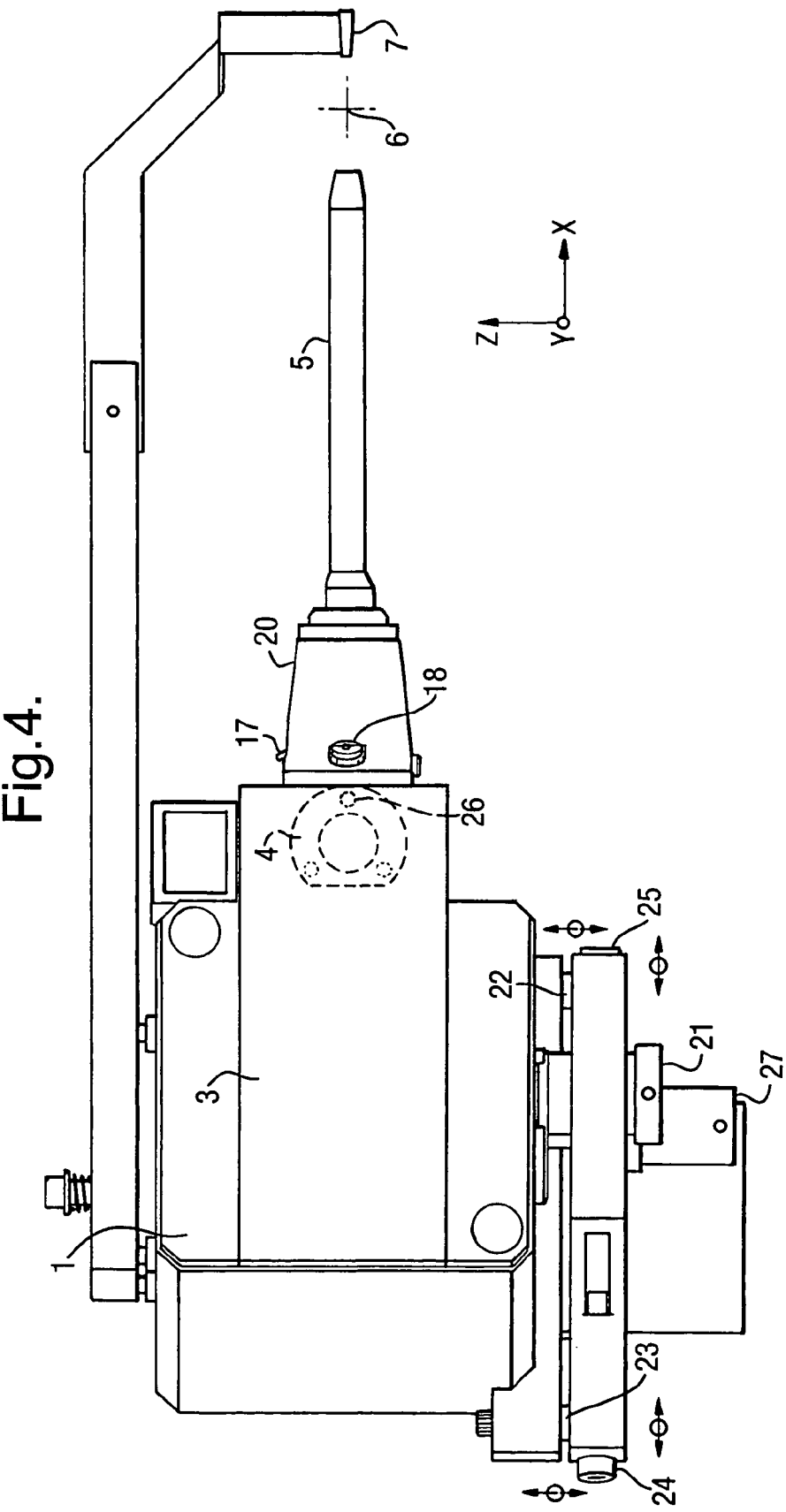
FIG. 4 is a side view of an arrangement in accordance with the present invention.

FIGS. 1 and 2 illustrate a prior art arrangement of x-ray optics components. The arrangement includes an x-ray source 1 which emits an x-ray beam from a focal spot 2; a shutter 3 for isolating the source; a monochromator 4 for generating a monochromatic x-ray beam from the incident beam generated by the source 1; a collimator 5 arranged to collimate the beam from the monochromator 4 onto a sample 6; and a beam stop 7.

The x-ray source 1 is a sealed tube inducing an electron gun and a target such as molybdenum or copper which generates x-rays when bombarded with electrons from the electron gun. The x-ray source 1 generates an x-ray beam from focal spot 2, which passes through the shutter 3 and is reflected from the monochromator 4 as a monochromatic beam, which enters the collimator 5 and is directed onto the sample 6. The collimator 5 is a standard pin hole type collimator having an entry pin hole 8 and an exit pin hole 9. The amount of flux which is lost due to divergence of the beam is dependent on the distances DM, being the distance from the focal spot 2 to the monochromator 4, and DS being the distance from the monochromator 4 to the sample 6.

In the prior art arrangement of FIGS. 1 and 2, the x-ray source 1 is movable linearly in both the Y and Z directions by means of the Y shift 10 and the Z shift (not shown). The source 1 is also rotatable about its Z axis, to vary the angle of incidence of the x-ray beam on the monochromator 4 which is mounted such that it can be tilted about the X axis by means of screws 12, 13 to achieve a Y-Z tilt, and about the Z axis by screw 14 to achieve a X-Y tilt. The monochromator 4 can also be linearly moved in both the Y and Z directions. The collimator 5 may be shifted in the Z direction by screws 12 and the Z direction by screws 16.

FIGS. 3 to 6 illustrate an arrangement of x-ray optics in accordance with the present invention. In this arrangement, the source 1, the shutter 3, the monochromator 4 and a collimator holder 20 are factory integrated and fixed with respect to each other. The collimator 5 is a mono-capillary type collimator, and the collimator 5 fits into the collimator holder 20, but is removable to allow it to be interchanged with collimators having different bore diameters or lengths. In this arrangement, the source 1, and the monochromator 4 are fixed with respect to each other, although the monochromator 4 can be adjusted to tilt around the Z axis by pins 26 to vary the angle of incidence of the beam on the monochromator 4. The collimator 5 is mounted in the collimator holder 20 in a joy-stick type arrangement, and it is adjusted by screws 17, 18 to tilt in the X-Z and X-Y planes respectively. In operation, the flux can be maximised by adjustment of the angle of the monochromator 4 and the direction of the collimator 5. The entire apparatus can then be shifted to direct the beam onto the sample 6. The entire arrangement may be shifted along the Z axis by screw 21, and can be tilted around the Y axis by screws 22, 23 and the Z axis by screws 24, 25. The locking screw 27 locks the Z shift and Y tilt after these adjustments have been made.

As can be seen, the distances DM and DS are much shorter in this arrangement than in the prior art, due to the integration of the components. Furthermore, much fewer adjustments are required to maximise the flux and aim the beam at the sample 6, and the adjustments can be carried out in a step by step fashion, as follows:

1) the monochromator 4 is adjusted without a collimator mounted in the collimator holder 20 to obtain the maximum flux using pins 26;

2) the collimator 5 is mounted in the collimator holder 20 and adjusted using screws 17 and 18 to obtain maximum flux through the collimator 5;

3) the beam is aimed onto the sample using the beam tilt screws 22, 23, 24, 25 and the beam shift 21.

The mono-capillary collimator 5 has a particular length, aperture and position such that the outer-most annulus of the beam entering the mono-capillary is, via a single bounce at less than a critical angle, redirected to the centre of the unintercepted central part of the beam, such that the intersection is at the sample position 6. In this way, the outer annulus of the beam, which is normally lost to the experiment, adds to the flux, which conserving the divergence.

Grazing incidence optics using capillaries have previously been used for x-ray work in other fields such as material research, medical applications, long wavelength studies etc. The principle is well known and is illustrated by FIG. 12, in its application to x-ray crystallography. For this example, the calculations will be based on a copper radiation source (CuK$\alpha$=1.54 Å). The external reflection angle for silica glass $\theta$=0.22°, and the diameter of the capillary $d_0$=0.5 mm. To achieve a single bounce in the mono-capillary before focussing the outer beam on the sample S, $$L_0 = \frac{d_0}{\tan\theta}$$

which for the above values will give $L_0$ approximately equal to 130 mm. Although the focusing effect could be achieved by multiple reflections in the mono-capillary, it is preferable to only have a single reflection because with each reflection power is lost due to absorption. It is preferable that only a portion L of the collimator is a mono-capillary, as shown in FIG. 7A. FIG. 7B illustrates a collimator in which the entire length $L_0$ is a mono-capillary and it can be seen that rays entering at the beginning of the collimator are reflected. In the embodiment of FIG. 7A, the rays entering at the beginning of the collimator are not reflected and are lost such that they do not add to the beam. However, the extra intensity is not required as it will be added around the sample thus creating unnecessary background.

FIG. 8 shows the Gaussian distributions of the beam which are obtained using different values of L. The profile using a standard pinhole collimator is also shown. It can be seen that the optimum value for L is between one third $L_0$ and one half $L_0$ The distance $L_0$ of the sample to the end of the capillary is optimised such that the sample is located slightly before the focal spot of the beam. The choice of capillary diameter/length will depend on the needed application and what size crystals are to be evaluated.

Figures 9, 10A, 10B:
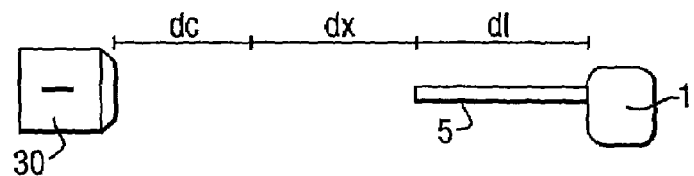
FIG. 9 illustrates an experimental set-up for monitoring the X-ray intensity profile.
FIG. 10A shows a comparison of intensity profiles for a 0.5 mm bore diameter collimator.
FIG. 10B shows a comparison of intensity profiles for a 0.8 mm bore diameter collimator.
Figure 11A:
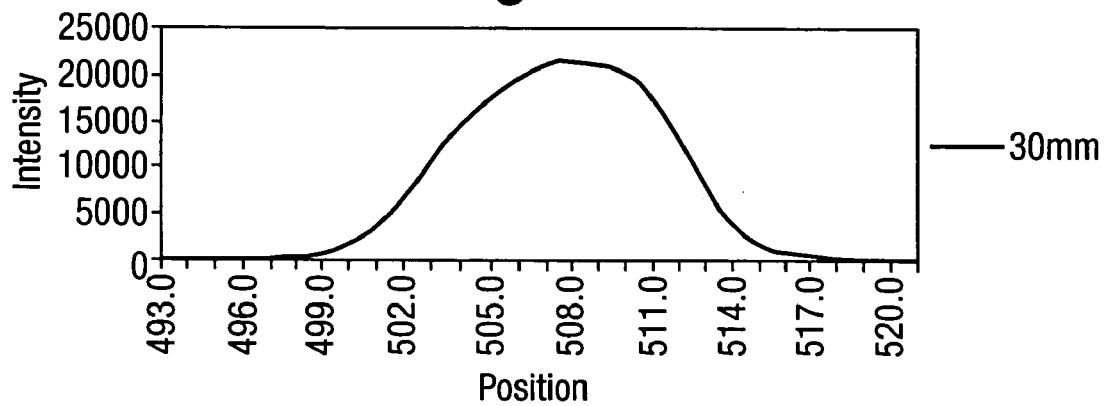
FIGS. 11A to 11E show graphically the intensity profiles at varying distances for a 0.5 mm bore diameter collimator in a set up according to the present invention.
Figure 11B:
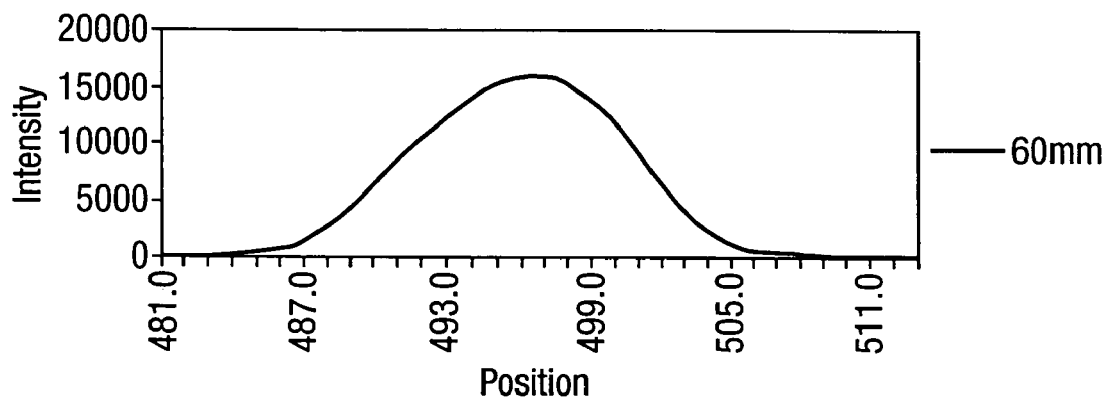
Figure 11C:
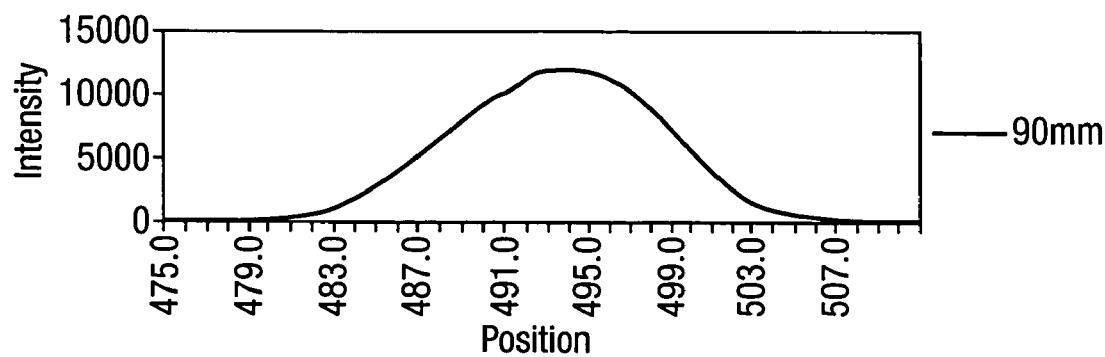
Figure 11D:
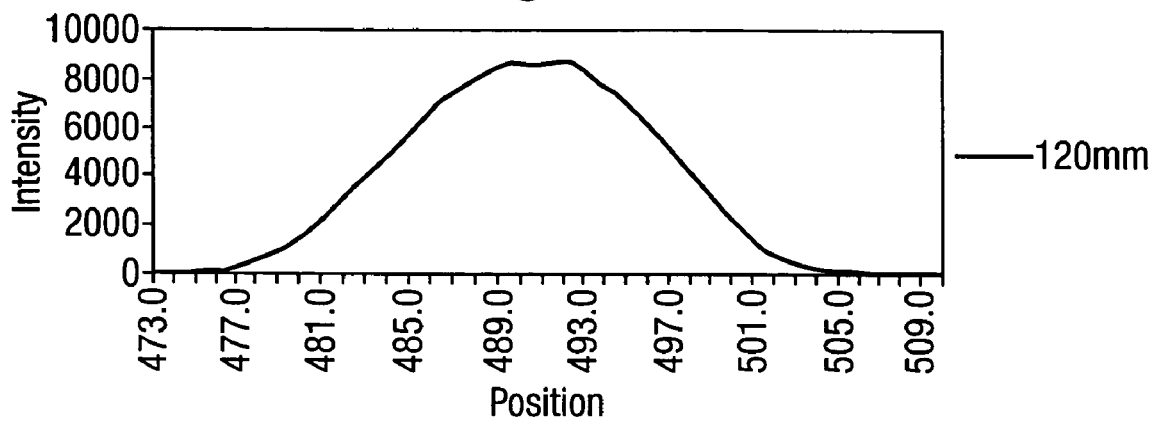
Figure 11E:
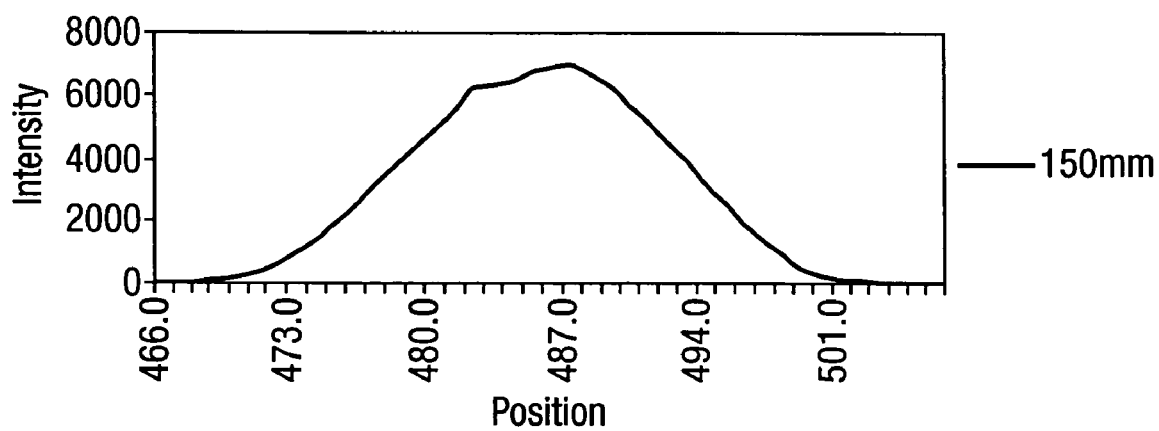
Figure 12A:
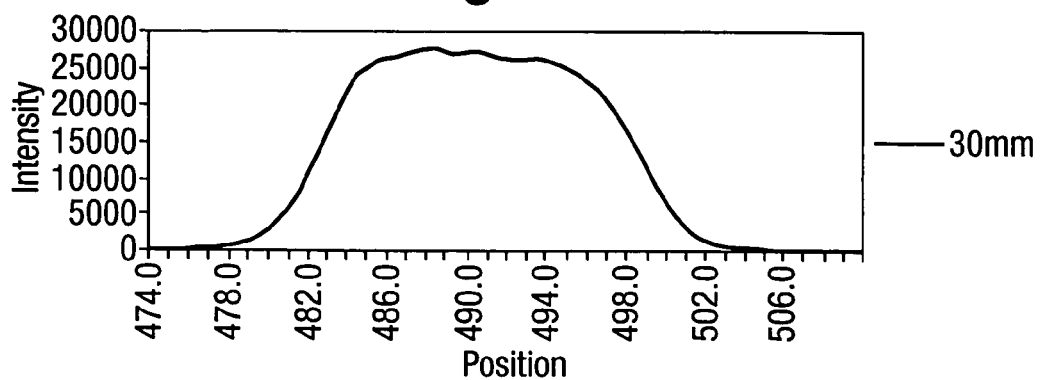
FIGS. 12 to 12E show graphically the intensity profiles at varying distances for a 0.8 mm bore diameter collimator in a set up according to the present invention; and, FIGS. 13A to 13E show intensity profiles graphically at varying distances for a prior art set-up with a 0.5 mm bore diameter collimator.
Figure 12B:
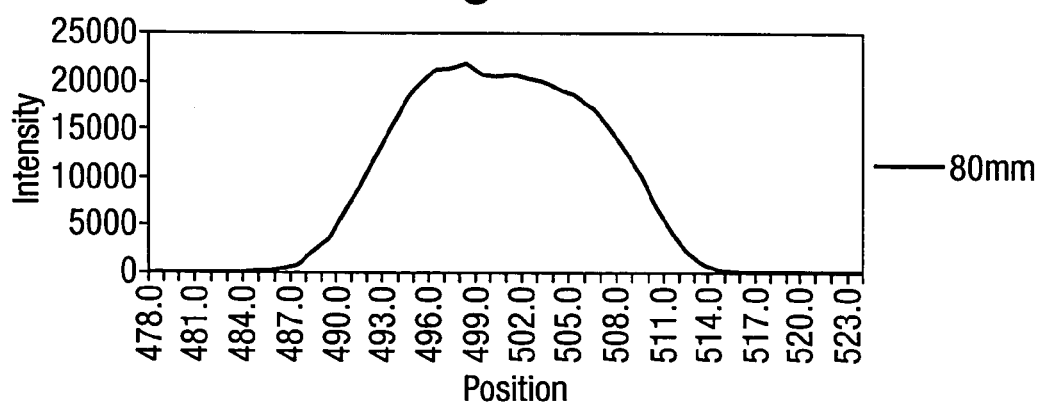
Figure 12C:
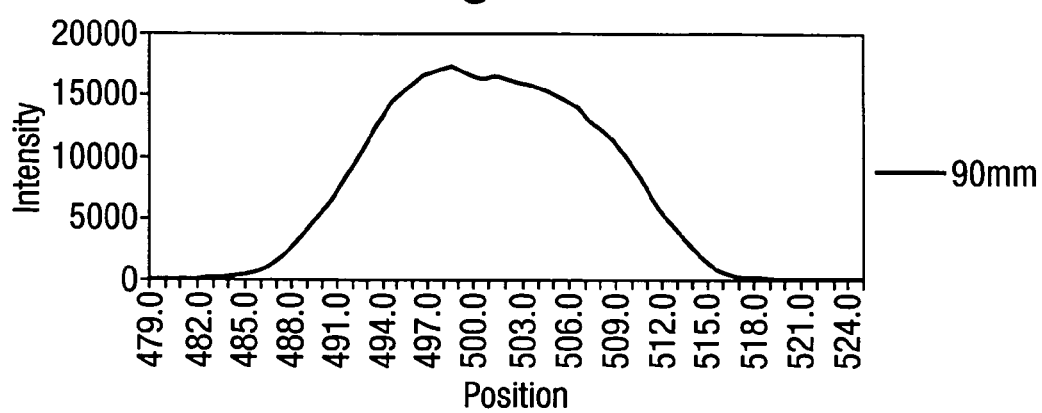
Figure 12D:
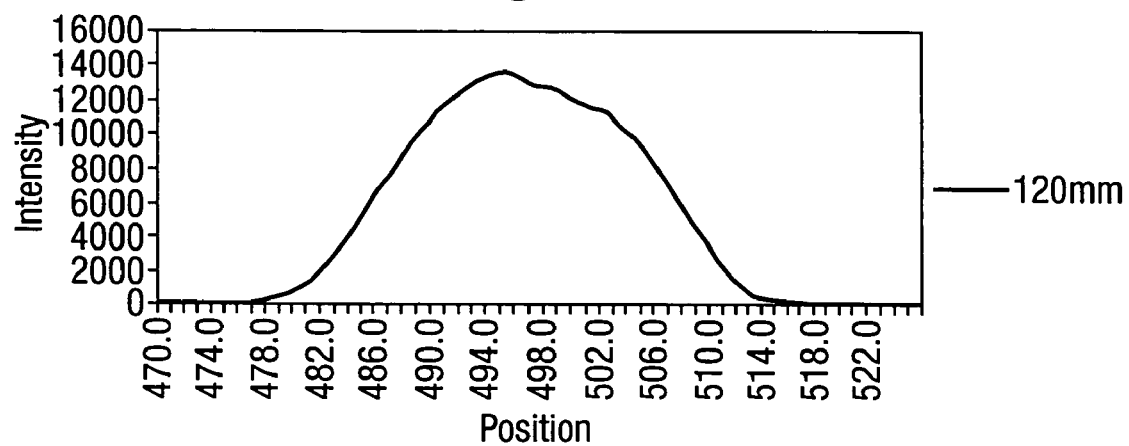
Figure 12E:
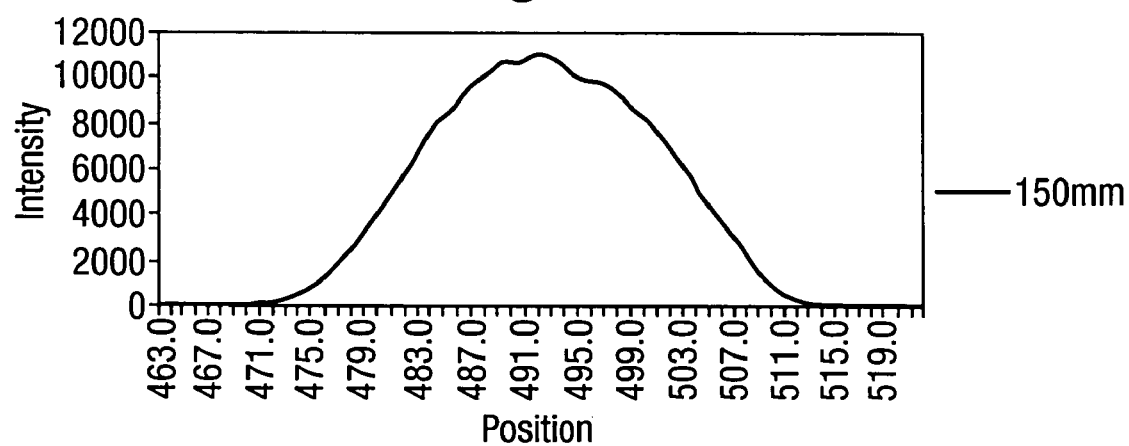
Figure 13A:
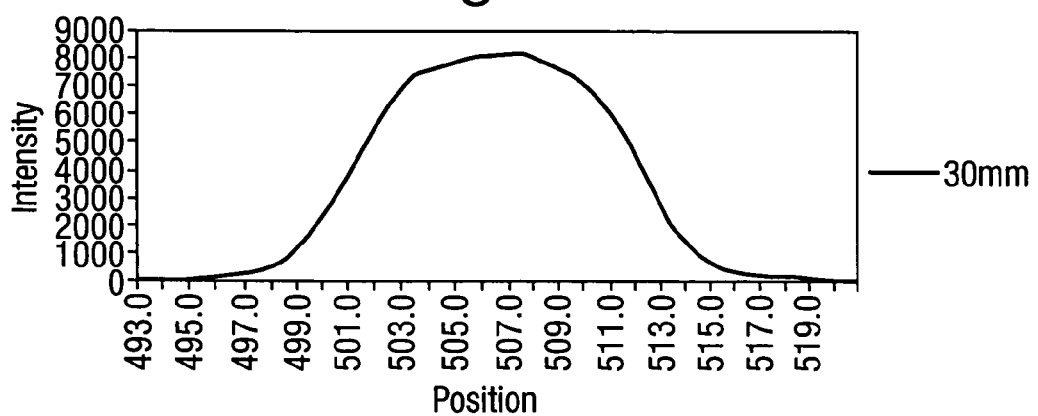
Figure 13B:
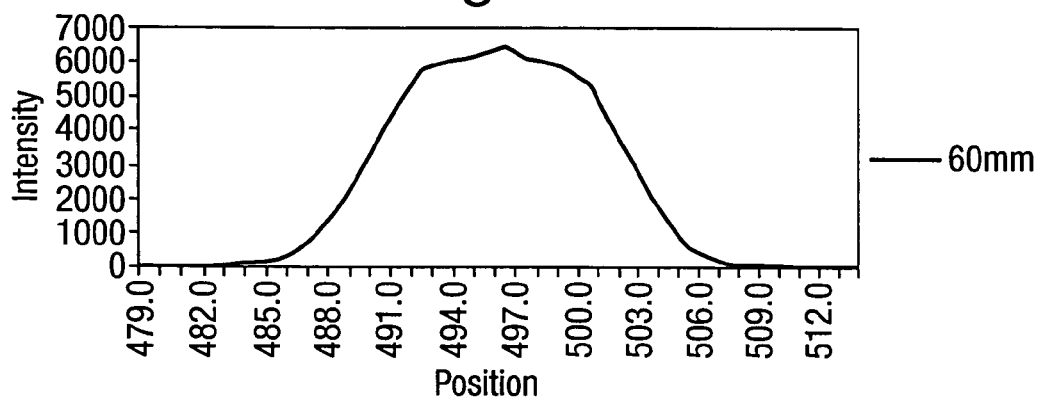
Figure 13C:
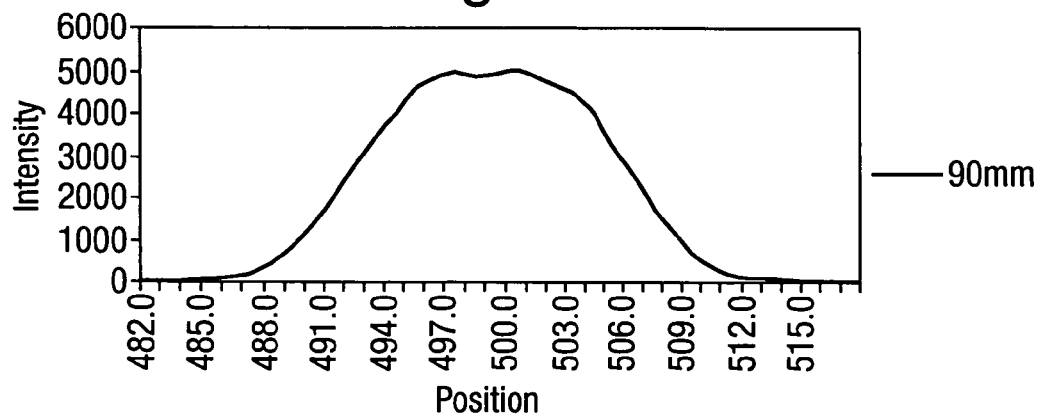
Figure 13D:
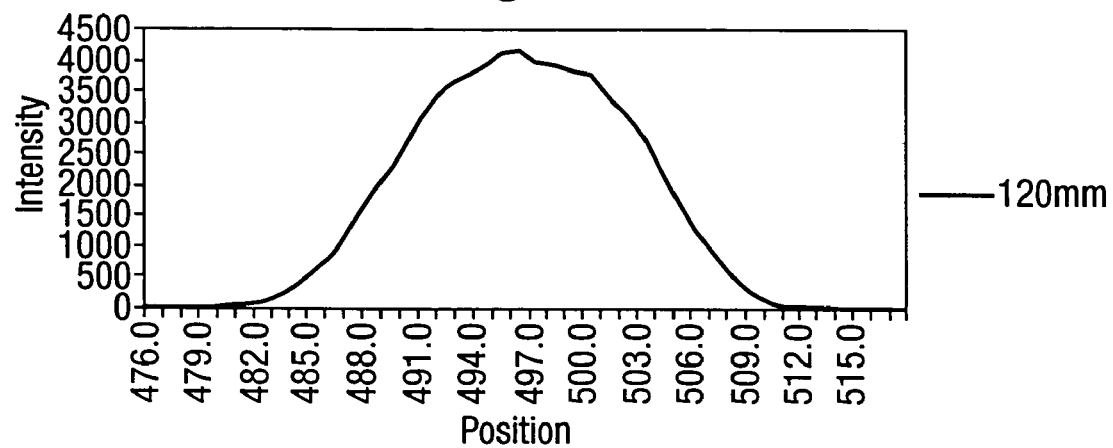
Figure 13E:
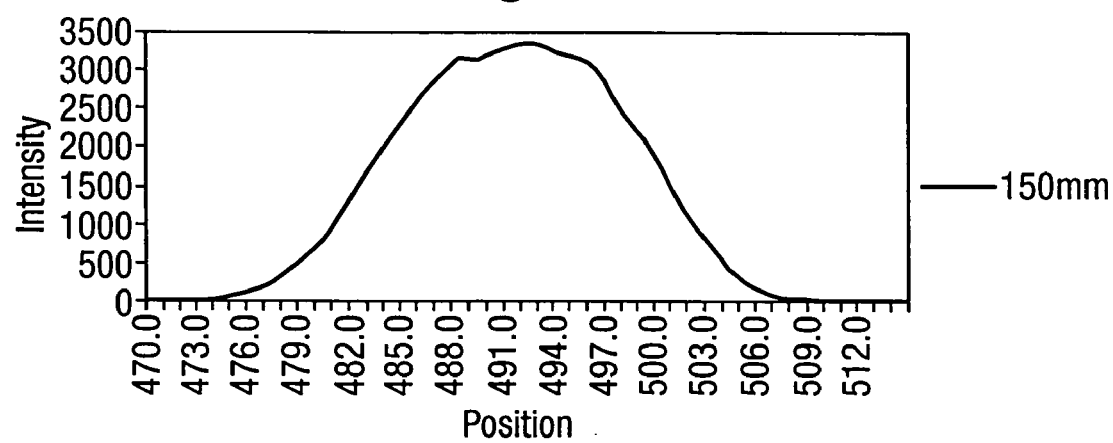

The apparatus was set up as shown in FIG. 9, with the x-ray optical assembly having the collimator 5 directed at a CCD camera 30. The distance dc represents the distance of the camera from the centre of the goniometer. The goniometer is the part of the diffractometer which is used to orient the crystal sample so that a chosen x-ray diffracted beam can be received by the detector, and it consists of four axes which allow the crystal sample to be rotated within a fixed area of 3D space so that the x-ray beam impinges and passes through any selected face of the sample. The goniometer is usually computer controlled. The distance from the end of the collimator 5 to the centre of the goniometer dx was set to be approximately 15 mm, and the length dl of the collimator 5 was approximately 120 mm. The CCD camera used has a resolution of 1024×1024 pixels, each pixel being a square with dimensions 0.06 mm×0.06 mm. FIG. 10A shows a comparison of intensity profiles of the beam at different distances dc for the prior art set up (REF) and the present invention (ENOX), both using a collimator having a 0.5 mm aperture. FIG. 10B shows the corresponding results for a 0.8 mm aperture collimator. As can clearly be seen, with the apparatus of the present invention, the intensity of the beam in the central region is maintained at much greater distances than with the prior art set up. It was found that the gain in monochromatic x-ray flux at the crystal sample position of the system according to the present invention compared to prior art system is between a factor of 2 and 2.5 for collimator apertures of between 0.5 and 0.8 mm.

FIGS. 11A to 11E illustrate the intensity profile of the beam graphically at distances of 30 mm, 60 mm, 90 mm, 120 mm and 150 mm respectively for the system of the present invention with a 0.5 mm collimator. FIGS. 12A to 12E show the corresponding results for a 0.8 mm collimator, and FIGS. 13A to 13E show the results for a 0.5 mm collimator in a standard prior art set up.

The invention claimed is:

1. An x-ray diffraction apparatus comprising:
an x-ray source for generating an x-ray beam;
a monochromator arranged to receive the x-ray beam and to generate a monochromatic x-ray beam from said x-ray beam, wherein the monochromator and the x-ray source are pre-assembled and mounted with respect to each other in an integrated unit such that in use the path length of the x-ray beam from the source to a point on the monochromator is maintained substantially constant; and,
a collimator arranged to receive the monochromatic x-ray beam, the collimator having a section towards the end proximate the sample position which includes a mono-capillary, wherein an outer diverging region of the monochromatic x-ray beam entering the collimator is reflected only once from an internal surface of the monocapillary so as to be directed to a sample position, and wherein the monocapillary section of the collimator extends over less than half the total length of the collimator.

2. An apparatus according to claim 1, adapted such that the angle of incidence of the x-ray beam on the monochromator may be varied.

3. An apparatus according to claim 2, in which the collimator is mounted such that the angle of the longitudinal axis of the collimator is variable with respect to the monochromator.

4. An apparatus according to claim 3, in which the angle can be varied in two orthogonal planes.

5. An apparatus according to claim 2, in which the collimator is mounted such that the direction of its longitudinal axis passes substantially through the centre of the monochromator.

6. An apparatus according to claim 5, in which the collimator is mounted in a socket in a collimator holder.

7. An apparatus according to claim 6, in which the integrated unit also includes a shutter located between the x-ray source and the monochromator such that the x-ray source can be isolated, and in which the collimator holder is integrated with the unit comprising the source, the monochromator and the shutter.

8. An apparatus according to claim 1, in which the monochromator is rotatable on an axis passing through it.

9. An apparatus according to claim 1, in which the integrated unit also includes a shutter located between the x-ray source and the monochromator such that the x-ray source can be isolated.

10. An apparatus according to claim 1, in which the collimator is mounted such that the angle of the longitudinal axis of the collimator is variable with respect to the monochromator.

11. An apparatus according to claim 10, in which the angle can be varied in two orthogonal planes.

12. An apparatus according to claim 1, in which the collimator is mounted such that the direction of its longitudinal axis passes substantially through the centre of the monochromator.

13. An apparatus according to claim 12, in which the collimator is mounted in a socket in a collimator holder.

14. An apparatus according to claim 13, in which the integrated unit also includes a shutter located between the x-ray source and the monochromator such that the x-ray source can be isolated, and in which the collimator holder is integrated with the unit comprising the source, the monochromator and the shutter.

15. An x-ray diffraction apparatus according to claim 1, wherein the monocapillary is cylindrical.

16. An x-ray diffraction apparatus comprising:
an x-ray source for generating an x-ray beam;
a monochromator arranged to receive the x-ray beam and to generate a monochromatic x-ray beam from said x-ray beam, wherein the monochromator and x-ray source are pre-assembled and mounted with respect to each other in an integrated unit such that in use the path length of the x-ray beam from the source to a point on the monochromator is maintained substantially constant; and
a collimator arranged to receive the monochromator x-ray beam, the collimator comprising a tube having a section towards the end proximate the sample position which includes a non-tapered monocapillary, wherein a first outer diverging region of the monochromatic x-ray beam entering the collimator is not reflected by the monocapillary and a second outer diverging region of the monochromatic x-ray beam entering the collimator is reflected only once from an internal surface of the monocapillary so as to be directed to a simple position, and wherein the monocapillary section of the collimator extends over less than half the total length of the collimator.

* * * * *